United States Patent [19]

Höök et al.

[11] Patent Number: 5,440,014
[45] Date of Patent: Aug. 8, 1995

[54] FIBRONECTIN BINDING PEPTIDE

[76] Inventors: Magnus Höök, 129 Stevens Hill Cir., Birmingham, Ala. 35244; Martin McGavin, 1717 Beacon Crest Cir., Birmingham, Ala. 35209; Guiseppe Raucci, Via Tito Speri 10, I-00040 Pomezia, Rome, Italy

[21] Appl. No.: 234,622

[22] Filed: Apr. 28, 1994

Related U.S. Application Data

[63] Continuation of Ser. No. 55,783, May 3, 1993, abandoned, which is a continuation of Ser. No. 846,995, Jun. 8, 1992, abandoned.

[30] Foreign Application Priority Data

Aug. 10, 1990 [SE] Sweden ............................ 9002617

[51] Int. Cl.$^6$ ............... A61K 38/00; C07K 1/00; C07K 7/08; C07K 14/00
[52] U.S. Cl. ..................... 530/326; 514/13
[58] Field of Search .................. 530/326; 514/13

[56] References Cited

U.S. PATENT DOCUMENTS

| | | | |
|---|---|---|---|
| 3,917,818 | 11/1975 | Botes | 424/87 |
| 4,312,942 | 1/1982 | Blobel et al. | 435/7 |
| 4,425,330 | 1/1984 | Norcross et al. | 424/92 |
| 4,645,757 | 2/1987 | Hjerten et al. | 514/54 |
| 4,784,989 | 11/1988 | Hook et al. | 514/21 |
| 4,795,803 | 1/1989 | Lindberg et al. | 530/324 |

FOREIGN PATENT DOCUMENTS

| | | |
|---|---|---|
| 0163623 | 12/1985 | European Pat. Off. |
| 0294349 | 7/1988 | European Pat. Off. |
| 0342173 | 11/1989 | European Pat. Off. |
| 0343137 | 11/1989 | European Pat. Off. |
| 0397633 | 11/1990 | European Pat. Off. |
| WO-A1-85/05553 | of 0000 | WIPO |
| WO-85/05037 | 11/1985 | WIPO |
| 9202555 | 2/1992 | WIPO |

OTHER PUBLICATIONS

Abrahmsen et al.—*Nucl. Acid Res.* 14(18):7487–7500 (1986).
Chhatwal et al.—*Comp. Immunol. Microbiol. Infect. Dis.* 10(2):99–108 Abstract (1987).
Duggleby et al.—*Nuc. Acid. Res.* 11(10):3065–3076 (1983).
Espersen et al.—*infect. and Immun.* 37(2):526–531 (Aug. 1982).
Flock et al.—*EMBO J.* 6 (8):2351–2357 (1987).
Froman et al.—*J. Biol. Chem.* 262(14):6564–6571 (1987).
Keil-Dlouha et al.—*Biochem. Biophys. Acta.* 727:115–21 (1983).
Lofdahl et al.—*Proc. Natl. Acad. Sci.* 80:697–701 (Feb. 1983).
Mamo et al.—*Micro. Pathog.* 2(6):417–424 Abstract (1987).
Myhre—*J. Med. Microbiol.* 18(2):189–196 Abstract (1984).
Myhre et al.—*Infect. Immun.* 40(1):29–34 (1983).
Nuesch et al.—*Gene* 32:243–249 (1984).
Overbeeke et al.—*J. Mol. Biol.* 163:513–532 (1983).
Ryden et al.—*J. Biol. Chem.* 258(5):3396–3401 (Mar. 1983).
Sambrook et al.—*Molecular Cloning: a Laboratory Manuel,* (2d), 6.39–6.43, B.9 (1989).
Switalski et al.—*Eur. J. Clin. Microbiol.* 1:381–387 (1982).
McGavin et al, J. Biol Chem, vol. 266, No. 13, pp. 8343–8347, 1991.
Signas, et al, Proc. Natl. Acad Sci. USA, vol. 86 pp. 699–703, 1989.

*Primary Examiner*—Jill Warden
*Assistant Examiner*—S. G. Marshall
*Attorney, Agent, or Firm*—Burns, Doane, Swecker & Mathis

[57] ABSTRACT

A fibronectin binding peptide having the structure R'-PSYQFGGHNS VDFEEDT-R$^2$ wherein R' is hydrogen, K or DK, and R$^2$ is hydroxy, L, LP or LPK is disclosed. The fibronectin binding proteins of the present invention may be used, for example, for vaccination of ruminants against mastitis caused by Staphylococcal infections, for the treatment of wounds, e.g., for blocking protein receptors or for immunization (vaccination) against infection by bacterial strains, and for diagnosis of bacterial infections caused by Staphylococci strains.

1 Claim, 6 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear     ( i i ) MOLECULE TYPE: peptide     ( i x ) FEATURE:
        ( A ) NAME/KEY: Peptide
        ( B ) LOCATION: 1
        ( D ) OTHER INFORMATION: /note="Amino acid 1 is R'wherein
            R'is hydrogen, K or DK."

( i x ) FEATURE:
        ( A ) NAME/KEY: Peptide
        ( B ) LOCATION: 19
        ( D ) OTHER INFORMATION: /note="Amino acid 19 is R2 wherein
            R2 is hydroxy, L, LP or LPK."

( x i ) SEQUENCE DESCRIPTION: SEQ ID NO:1:

Xaa  Pro  Ser  Tyr  Gln  Phe  Gly  Gly  His  Asn  Ser  Val  Asp  Phe  Glu  Glu
1                       5                            10                        15

Asp  Thr  Xaa ( 2 ) INFORMATION FOR SEQ ID NO:2:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:2:

```
        Gln  Asn  Ser  Gly  Asn  Gln  Ser  Phe  Glu  Glu  Asp  Thr  Glu  Glu  Asp  Lys
         1             5                        10                           15

Pro  Lys  Tyr  Glu  Gln  Gly  Gly  Asn  Ile  Val  Asp  Ile  Asp  Phe  Asp  Ser
                       20                       25                      30

Val  Pro  Gln  Ile  His  Gly
                       35
```

( 2 ) INFORMATION FOR SEQ ID NO:3:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:3:

```
        Gln  Asn  Lys  Gly  Asn  Gln  Ser  Phe  Glu  Glu  Asp  Thr  Glu  Lys  Asp  Lys
         1             5                        10                           15

Pro  Lys  Tyr  Glu  His  Gly  Gly  Asn  Ile  Ile  Asp  Ile  Asp  Phe  Asp  Ser
                       20                       25                      30

Val  Pro  His  Ile  His  Gly
                       35
```

( 2 ) INFORMATION FOR SEQ ID NO:4:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:4:

```
        Phe  Asn  Lys  His  Thr  Glu  Ile  Ile  Glu  Glu  Asp  Thr  Asn  Lys  Asp  Lys
         1             5                        10                           15

Pro  Ser  Tyr  Gln  Phe  Gly  Gly  His  Asn  Ser  Val  Asp  Phe  Glu  Glu  Asp
                       20                       25                      30

Thr  Leu  Pro  Lys  Val
                       35
```

FIBRONECTIN BINDING PEPTIDE

This application is a continuation, of application Ser. No. 08/055,783, filed May 3, 1993, now abandoned, and which is a continuation of application Ser. No. 07/846,995, filed Jun. 8, 1992, now abandoned.

DESCRIPTION

1. Technical field

The present invention relates to a fibronectin binding peptide.

The object of the present invention is to obtain a minimal fibronectin binding polypeptide.

A further object is to obtain a possibility of preparing said peptide by chemical synthesis. Further objects will be apparent from the following description.

BACKGROUND OF THE INVENTION

WO-A1-85/05553 discloses bacterial cell surface proteins having fibronectin, fibrinogen, collagen, and/or laminin binding ability. Thereby it is shown that different bacteria have an ability to bind to fibronectin, fibrinogen, collagen, and/or laminin. It is further shown that fibronectin binding protein has a molecular weight of 165 kD and/or 87 kD, whereby it is probable that the smaller protein is a part of the larger one.

Fibronectin is a disulfide linked dimeric glycoprotein (M=450,000) which is present in a soluble form in blood plasma and other body fluids, and is deposited in a fibrillar form as a major constituent of the extracellular matrix of loose connective tissue. It is composed of three different structural motifs, termed type I, II, and III homologies (Petersen et al., 1983; PNAS), resulting in a modular organization cf the fibronectin molecule in which its several biological activities can each be attributed to specific domains.

The major biological role of fibronectin appears to be related to its ability to mediate the adhesion of eukaryotic cells to the extracellular matrix through a specific interaction between discrete cell surface receptors, and a 105-kDa central region of the molecule composed entirely of type III homology units (Pierschbacher and Ruoslahti, 1984, Nature 309:30–33). The cell binding domain is succeeded at its C-terminal end by a 31 kDa heparin binding domain and a 30 kDa fibrin binding domain. Preceding the cell binding domain is a 42 kDa gelatin (collagen) binding domain, and an N-terminal 29 kDa domain consisting of five consecutive type I repeats that binds fibrin, heparin and bacteria (Yamada 1983, Ann. Rev. Biochem. 52:761–799).

Several pathogenic Gram-positive staphylococci and streptococci have been reported to bind exclusively to the 29-kDa N-terminal domain of fibronectin (Speziale et al., 1984, J. Bacteriol. 157:420–427, Mosher and Proctor, 1980 Science 209:927–929). Some of the Gram-negative enteric bacteria, namely *Escherichia coli, Salmonella typhimurium, S. enteritidis,* and *S. dublin* have also been reported to bind fibronectin (Froman et al., 1984, JBC 259:14899–14905; Van de Water et al., 1983, Science 220:201–204; Faris et al., 1986, FEM Microbiol. Lett. 34:221–224; Baloda et al., 1986, FEMS Microbiol. Lett. 34:225–229; Batoda et al., 1985, FEMS Microbiol. Lett. 28:1–5; Kristiansen et al., 1987), and it was reported for *E. coli,* that the bacteria bound to the 29 kDa N-terminal domain, and a second unidentified site (Froman et al., 1984). In contrast, the spirochete *Treponema palladium,* and the trypanosome *Trypanosoma cruzi* differ from other fibronectin binding microorganisms in showing a specificity for the 105 kDa eukaryotic cell binding domain (Thomas et al., 1985a, J. Exp. Med. 161:514–525; Ouaissi et al., 1986, J. Exp. Med. 162:1715–1719).

The dissociation constants for the interaction of these microorganisms with fibronectin show a $10^2$ to $10^3$-fold higher affinity than that reported for the binding of intact fibronectin to human fibroblasts (Hook et al., 1989; Akiyama and Yamada, 1985, JBC 260:4492–4500). This avidity for fibronectin may be a virulence factor, facilitating the colonization of wound tissues and blood clots, where a fibronectin rich matrix is known to be deposited during the first and second weeks of wound repair (Kurikinen et al., 1980, Lab Invest. 43:47–51; Grinell et al., 1981, J. Invest. Dermatol. 76:181–189; Clark et al., 1982, J. Invest. Dermatol. 79:269–276). It has been the intent of the present research to characterize microbial fibronectin binding proteins (FnBPs), and to develop receptor analogs for potential therapeutic application towards preventing or reducing the risk of wound infection.

Studies on FnBPs have so far mostly dealt with the FnBP of *S. aureus.* A FnBP with an M=of 210,000 has been reported from three laboratories (Espersen and Clemmensen, 1982, Infect. Immun. 37:526–531; Froman et al., 1987, J. Biol. Chem. 262:6564–6571; Signas et al., 1989, PNAS 86:699–703). The gene encoding the FnBP of *S. aureus* 8325-4 has been cloned and expressed in *E. coli* (Flock et al., 1987, EMBO J. 2351–2357). The fibronectin binding activity was localized to a 600 base pair insert, which when fused in frame with DNA coding for two IgG binding domains of staphylococcal protein A, yielded a protein fusion designated ZZ-FR which had the same fibronectin binding activity as the native 210 kDa receptor. Subsequent DNA sequence analysis revealed 600 base pair insert to code for 184 amino acids, of which a prominent feature was a 38 amino acid homology unit repeated three times, and partially a fourth (Signas et al., 1989).

It has been found that synthetic peptide analogs to each the homology units, designated D1, D2, and D3, were effective inhibitors of fibronectin binding to *S. aureus* 8325-4. Peptide D3 constructed on the third homology unit was 50 to 100-fold more effective as an inhibitor of fibronectin binding, but showed a considerable deviation from the basic homology unit. In the present invention it is further defined the fibronectin binding determinant within the D3 homology unit through means of chemical modification, proteolytic cleavage, and chemical synthesis of a number smaller peptides encompassing the D3 sequence.

DESCRIPTION OF THE PRESENT INVENTION

The present invention relates to a minimum fibronectin binding peptide having the structure [seq ID No. 1] R'-PSYQFGGHNSVDFEEDT-R² wherein R' is hydrogen, K or DK, and R=is hydroxy, L, LP, or LPK whereby A Ala, Alanine
R Arg, Arginine
N Asn, Asparagine
D Asp, Aspattic acid
C Cys, Cysteine
C Cys, Cystine
G Gly, Glycine
Glu, Glutamic acid
Q Gln, Glutamine
H His, Histidine I Ile, Isoleucine
L Leu, Leucine
K Lys, Lysine
M Met, Methionine
P Phe, Phenylalanine
P Pro, Proline
S Ser, Serine
T Thr, Threonine
W Trp, Tryptophan
Y Tyr, Tyrosine
V Val, Valine

MATERIALS AND METHODS

Bacteria and Growth Media

*Staphylococcus aureus* 8325-4, described by Lofdahl et al., (1983, PNAS USA 80: 697–701) was stored in deep agar at 40° C. Cultures were started by inoculation into Brain Heart Infusion broth (Difco, Detroit, Mich.). After overnight incubation at 37° C., the bacteria were collected by centrifugation, suspended in phosphate buffered saline 7.4), containing 0.02% (wt/vol) sodium azide, and adjusted to a value of $10^{10}$ cells/ml of suspension by reference to a standard curve relating cell count to optical density. The cells were then heat kolled at 88° C. for 20 minutes, aliquoted, and stored frozen at −20° C.

Preparation and Iodination of Ligands

Human fibronectin was either purchased from the New York Blood Center, or purified from outdated plasma obtained from the same source, as described by Engvall and Rouslahti (1977, Int. J. Cancer Res. 20:1–5). For purification of the 29-kDa N-terminal domain of fibronectin, human fibronectin was diluted to 1 mg/ml in a buffer consisting of 25 mM Tris-HCl (pH 7.6), 50 nM sodium chloride, 2.5 mM calcium chloride, and 0.5 mM ethylenediamine tetraacetic acid (EDTA). Protease digestion was initiated by addition of 5 μg of thermolysin (Calbiochem, La Jolla, Calif.) for each 1 mg of fibronectin, followed by incubation for 2 hours at room temperature with end over end mixing. The reaction was stopped by addition of EDTA to 5 mM. The 29 kDa fragment was then isolated by passage of the digest through an affinity gel matrix consisting of ZZ-FR fusion protein (Flock et al., 1987) coupled to Sepharose CL-4B (Pharmacia, Uppsala, Sweden), and subsequently eluted with 4M guanidine hydrochloride in phosphate buffered saline (PBS). The eluate was then dialyzed extensively against PBS. Iodination of either fibronectin or the 29 kDa fragment was conducted according to the chloramine T protocol of Hunter (978).

Assay of Fibronectin Binding

Synthetic peptides were analyzed for fibronectin binding activity by measuring their ability to compete with cells of *S. aureus* 8325-4 for binding of $^{125}$I-labeled fibronectin, or labeled N-terminal 29 kDa fragment, exactly as described previously (Signas et al., 1989). Where indicated, this assay was modified by replacing the bacterial suspension with 40 1 of the ZZ-FR Sepharose (coupling ration of 0.3 mg/ml of swollen gel). In this case, the background radioactivity was determined from an assay in which unmodified Sepharose was used in place of the affinity matrix. Radiolabeled ligand bound either to bacteria or ZZ-FR Sepharose was quantitated in an LKB gamma counter (Turku, Finland).

Synthesis and Purification of Peptides

All peptides with the exception of S16–36 were synthesized on an Applied Biosystems automatic peptide synthesizer at the University of Alabama at Birmingham Cancer Center core facility as described previously (Signas et al, 1989). Peptide S16–36 was synthesized by Vega Biotechnotogies (Tucson, Ariz.) using an F-moc synthesis procedure. Peptides were purified from the crude preparations by reverse-phase HPLC using a preparative scale $C_{18}$ column (Vydac 218TP510; The Separation Group, Hesparia, Calif.) and an LKB HPLC system. The buffer used for the purification was TEAP/EDTA (pH 5.5), consisting of 0.11% (vol/vol) phosphoric acid, 0.28% (vol/vol) triethyamine, and 0.25 mM EDTA. The elution buffer was 15% of TEAP/EDTA in acetonitrile.

Triethylamine was purchased from Pierce (Rockford, Ill.), while HPLC grade phosphoric acid and acetonitrile was from Fisher (Pittsburgh, Pa.). After reverse-phase chromatography, the appropriate fractions were dialyzed extensively against 50 mM ammonium bicarbonate and lyophilized. The purity of the resulting preparations was checked by reverse-phase chromatography on an analytical $C_{18}$ column (vydac 218TP546; The Separation Group, Hesperia, Calif.) using a buffer consisting of 0.1% (vol/vol) trifluoroacetic acid (Pierce; Rockford, Ill. in water, and 0.1% (vol/vol) TFA in 60% acetonitrile as the elution buffer. Peptides eluting in this buffering system were dried by roto-evaporation and submitted for either N-terminal sequence analysis or amino acid composition analysis.

Peptide sequencing was done by the Protein Chemistry Core of the University of Alabama at Birmingham on an Applied Biosystems peptide sequencer, Model 470A. The amino acid analysis was done by %he Atherosclerosis Research Unit Protein Chemistry Core.

Proteolytic Digestion of Synthetic Peptides

L-(tosylamido-2-phenyl)-ethyl-chloromethyl-ketone (TPCK) treated trypsin (code TRTPCK) and chymotrypsin (code CDS) was obtained from Worthington (Freehold, N.J.). Soybean trypsin inhibitor and TPCK were purchased from Sigma (St. Louis, Mo.), endoproteinase Glu-c (V8 protease) was purchased from Boerhinger Mannheim and lysine endopeptidase C (LEC) was obtained from Calbiochem (La Jolla, Calif.).

For both trypsin and chymotrypsin digestion, peptide D3 was dissolved at 2 mg/ml in 0.1M ammonium bicarbonate and treated with protease at an enzyme to substrate ratio of 1:200 for 24 h ay 37° C. Trypsin was inactivated by addition of soybean trypsin inhibitor and phenylmethysulfonylftuoride tp 20 g/ml and 1 mM, respectively. For chymotrypsin, TPCK and PMSF were added to achieve concentrations of 0.3 mg/ml and 1 mM, respectively.

For endoproteinase Glu-c digestion, the enzyme to substrate ratio was 1:100 and peptide was 2 mg/ml in phosphate buffered saline. After incubation for 24th at room temperature, the digestion was stopped by addition of PMSF to 1 mM. For LEC digestion, peptide was dissolved in PBS at 2 mg/ml, to which was added 1 unit of protease per ml. Digestion was allowed to continue for 40 h at 37° C., and was terminated when the cleavage products were separated by HPLC. For each digestion, reverse-phase HPLC with the TEAP/EDTA buffer system was used to monitor the progress of proteolysis and to purify the cleavage products. Samples needed for composition analysis or N-terminal sequencing were further chromatographed with the TFA buffer system.

Chemical Modification of Synthetic Peptides

Dihydroxypropylation-reduction of the amino side chain of lysine was a modification of the method of Acharya (1984; J. Chrom. 297:37–38). Peptide was dissolved in PBS (2.5 mg/ml), followed by addition of DL-glyceraldehyde and sodium cyanoborohydride (Sigma, St. Louis, Mo.) to a final concentration of 0.1 and 1.0 molar, respectively. The reaction was conducted at room temperature for 1 h and was stopped by dialysis against 50 mM ammonium bicarbonate. The extent derivatization of lysine side residues was determined by amino acid analysis.

The carboxylic side chains of glutamic and aspartic residues were converted to glycine methyl esters by 1-ethyl-3(3-dimethylamino-propyl)-carbodiimide (EDC) mediated condensation (Lungblad and Noyes, 1985; Chemical Reagents for Protein Modification, Vol II). Peptide was dissolved in double distilled water an 2 mg/ml and rendered 1M in glycine methyl ester (Sigma). The pH was adjusted to 4.3 with 0.1M HCl and EDC was added to a concentration of 0.1M. The solution was mixed for 3 h at room temperature with adjustment of pH back to 4.3 after 30 min. and again after 1.5h. The reaction was stopped by dialysis against PBS. The degree of derivatization was determined by the increase of the glycine molar ratio as compared to the underivatized peptide. A derivatization was done in which ethanolamine was used in place of glycine methyl ester, and a control experiment was performed in which only EDC was mixed with the peptide.

The phenyl side chains of tyrosine residues were oxidized by addition of 10 μl of tetranitromethane (TNM; Sigma) to each ml of 1 mg/ml peptide dissolved in 100 mM Tris-HCl, 150 mM NaCl (pH 8.0), and mixing for 1 hr at room temperature, followed by dialysis against Tris/NaCl buffer (pH 8.0) to remove TNM.

Figure 1:
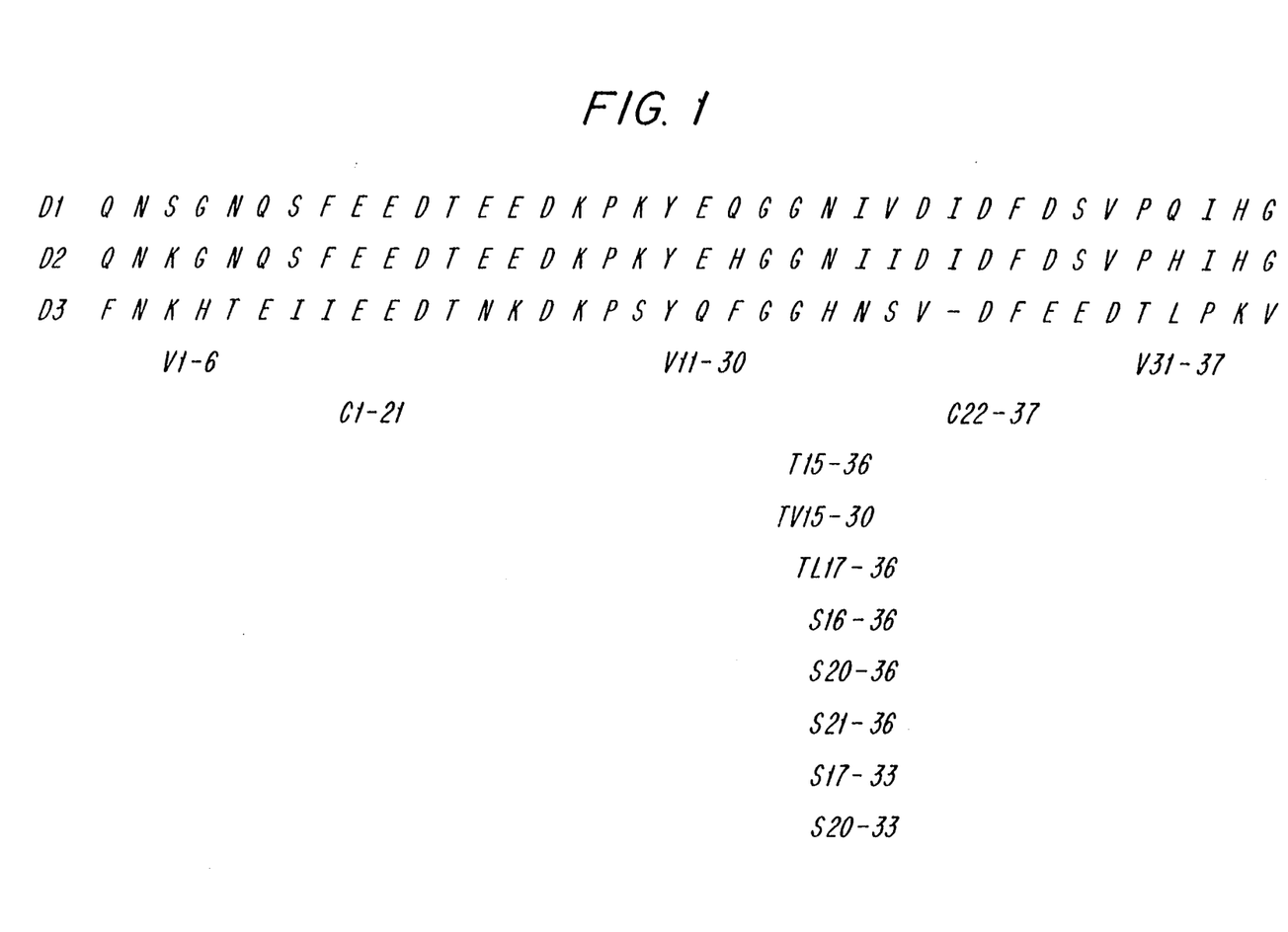

The amino acid sequence [Seq ID Nos. 2–4] of the three D-repeats is shown in FIG. 1. The D1 and D2 repeats show a high degree of homology differing in only 5 of 38 residues (87% homology), whereas D3 shows less than 50% homology with D2. However, as noted previously (Signas et al., 1989), the peptide affected a 50% inhibition of $^{125}$I-HFN binding to cells of *S. aureus* 8325-4 at a concentration of 2 g/ml, while concentrations of 90 g and 230 g/ml for D2 and D1, respectively, were required to give the same degree of inhibition. We, therefore, chose peptide D3 for further characterization.

Chemical Modification

Table 1 is composed on the data from amino acid composition analysis of peptide D3 and its derivatization products. Dihydroxypropylation of lysine side residues was quantitatively complete showing a greater than 98% reduction in lysine content in comparison to D3. A minor side reaction normally occurring through use of this protocol was the derivatization of phenylalanine in position 1 via its free NH$_2$ group, as noted by a slight decrease in phenylalanine content. Conversion of aspartic and glutamic residues to glycine methyl-ester was also quantitatively complete, as noted by the change in glycine content from 54 residues per 1,000 to 293. This is the value expected for the 2 glycine residues in D3, and the 9 additional residues which were added by complete chemical modification of the aspartic/glutamic residues. The TNM mediated oxidation of tyrosine was also successful showing a 95% reduction in tyrosine content.

Figure 2A:
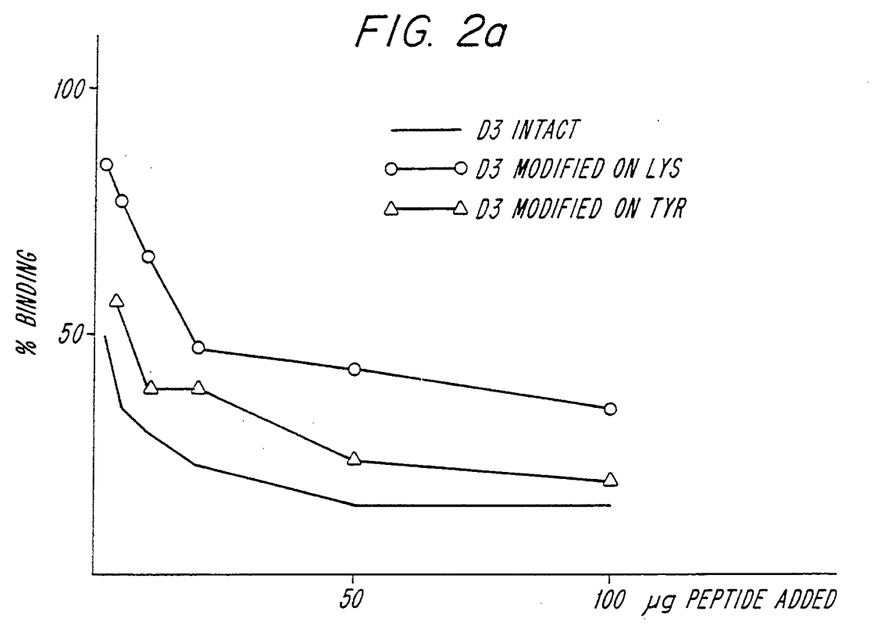
Figure 2B:
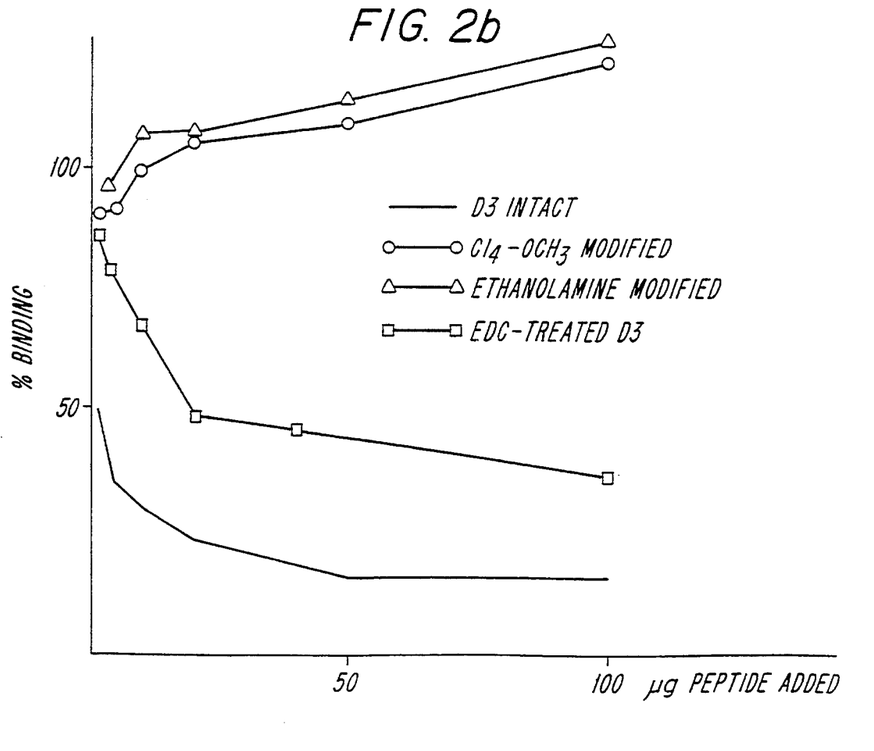

FIG. 2 shows the inhibition activity of the chemically modified peptides compared to that of unmodified D3. While lysine and tyrosine modifications only partially diminished the activity of D3, modification of aspartic/glutamic residues resulted in a total loss of activity. This result was observed with either glycine methyl ester or ethanolamine condensation on the carboxylic side chains. As a control, EDC treatment alone showed only a small loss in activity similar to that observed with the lysine and tyrosine modifications. The observed loss of activity is therefore due specifically to modification of carboxyl side chains.

Figure 3A:
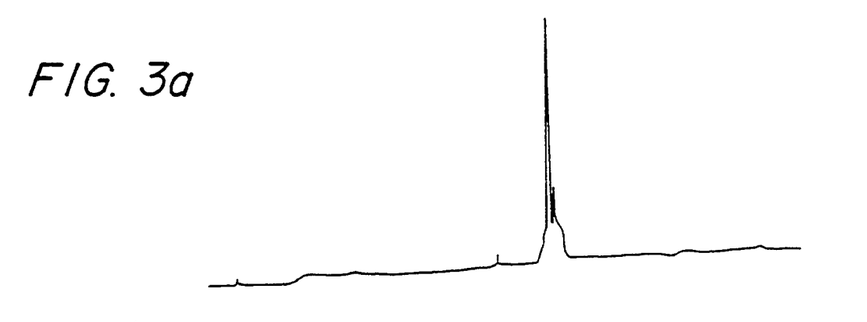
Figure 3B:
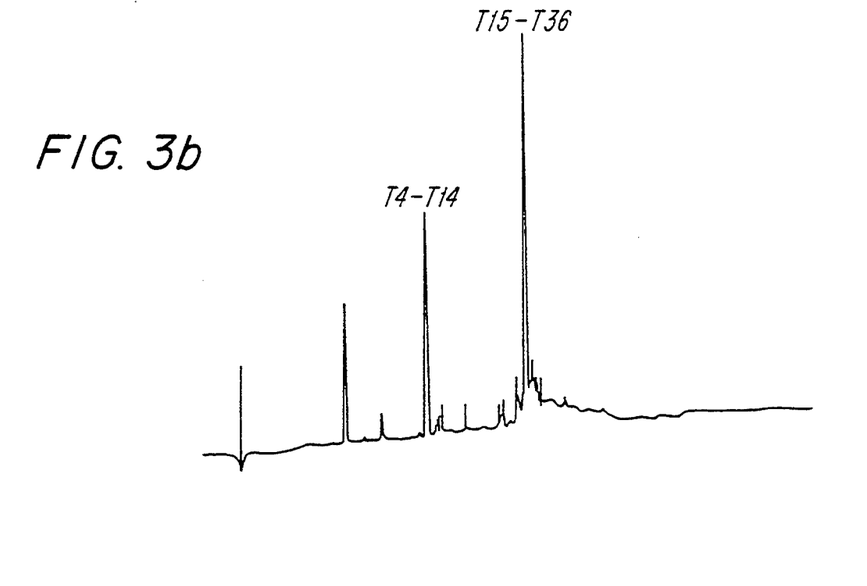
Figure 3C:
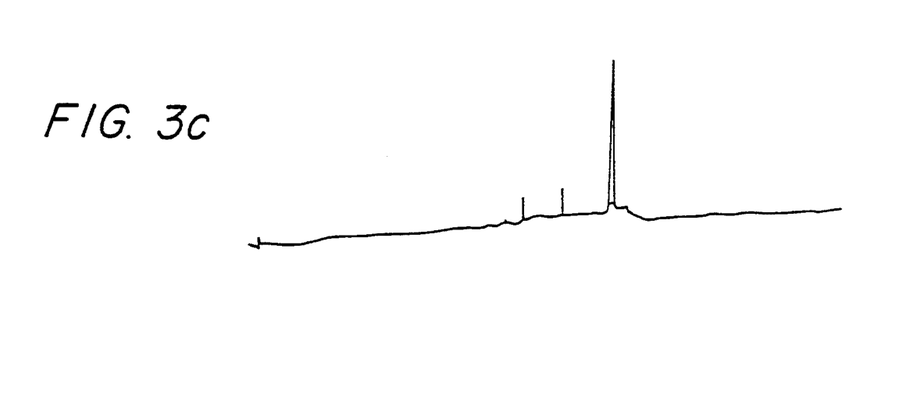
Figure 4A:
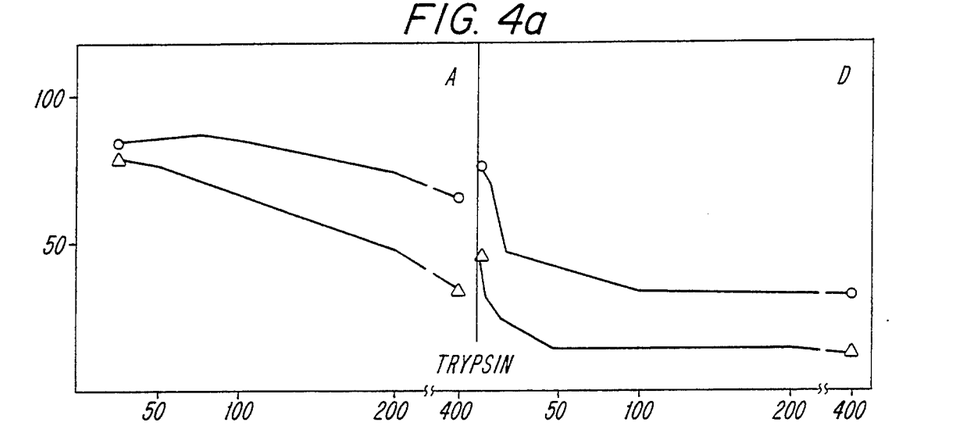
Figure 4B:
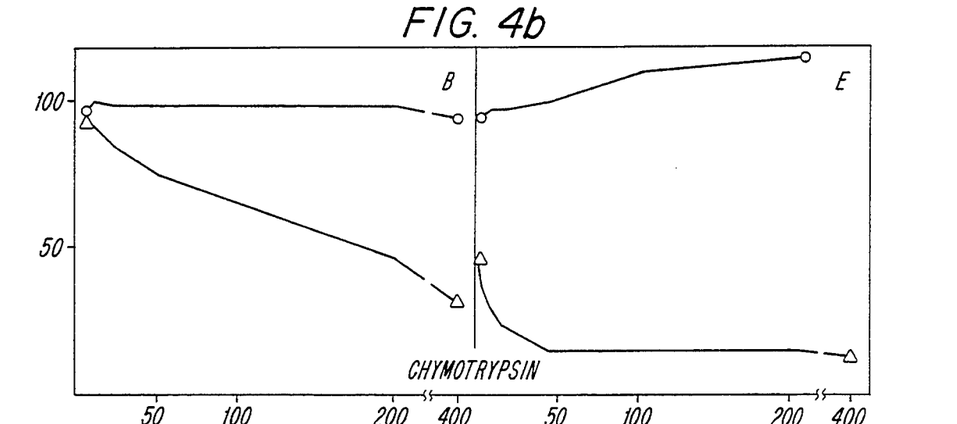
Figure 4C:
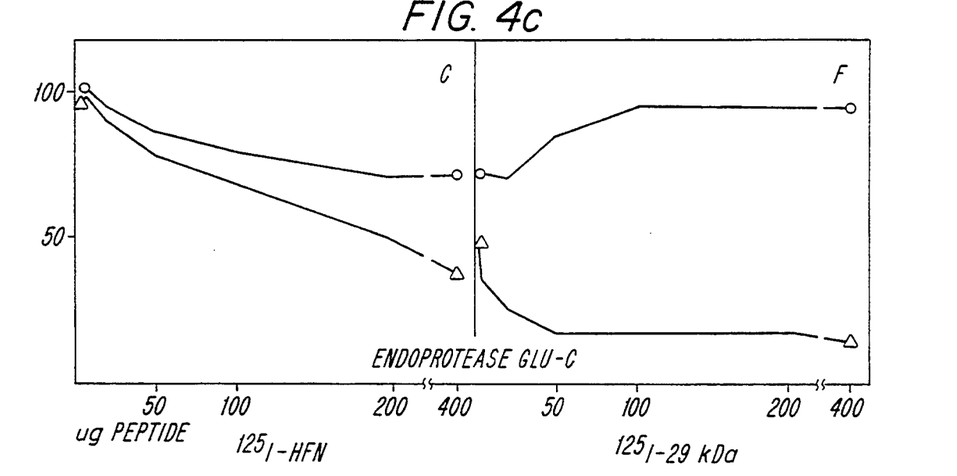

Reverse-phase HPLC of trypsin, chymotrypsin and endoprotease Glu-c digests of D3 confirmed that the peptide substrate was completely converted into smaller products. Representative reverse-phase profiles of D3 and its' tryptic digest are shown in FIG. 3, along with the identity of the fragments which were subsequently purified. Initial assays were conducted with the crude digests in the presence of appropriate protease inhibitors to test for banding of either $^{125}$I-HFN or the $^{125}$I-29 kDa N-terminal fragment to an *S. aureus* cell suspension (FIG. 4). After complete trypsin digestion, as verified in FIG. 3, the resulting unfractionated cleavage products showed little loss in biological logical activity, whereas the chymotrypsin digest showed no inhibitory activity. The results were less clear with the endoprotease Glu-c digest which showed inhibitory activity using $^{125}$I-29 kDa as the ligand, but none with $^{125}$I-HFN. This may be due to changes in conformation when the N-terminal domain is detached by proteolytic cleavage.

Figure 5:
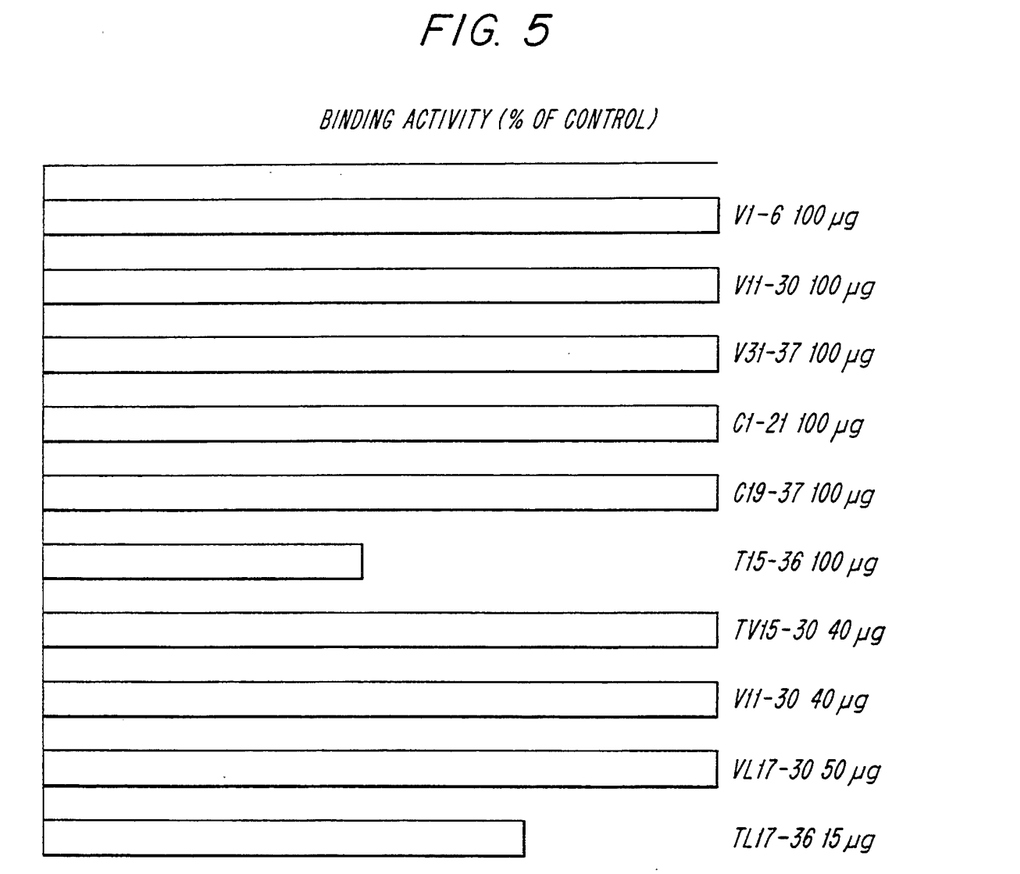

FIG. 1 shows the amino acid sequences of several cleavage products which were purified from the crude digests by reverse-phase HPLC. The major cleavage product purified from the trypsin digest constituted residues 15–36 (T15–36) of the 37 amino acid D3, and biological activity was retained by this peptide (FIG. 5). Further digestion of this peptide with lysine endopeptidase-c resulted in the removal of an N-terminal dipeptide producing TL17–36 which still showed inhibitory activity. Cleavage of T15–36 with endoprotease Glu-c resulted in removal of a C-terminalhexapeptide and concomitant loss of activity. The sequences of peptides isolated from endoprotease Glu-c and chymotrypsin digests of D3 are also given in FIG. 1. None of these peptides had inhibitory activity (FIG. 5).

Figure 6:
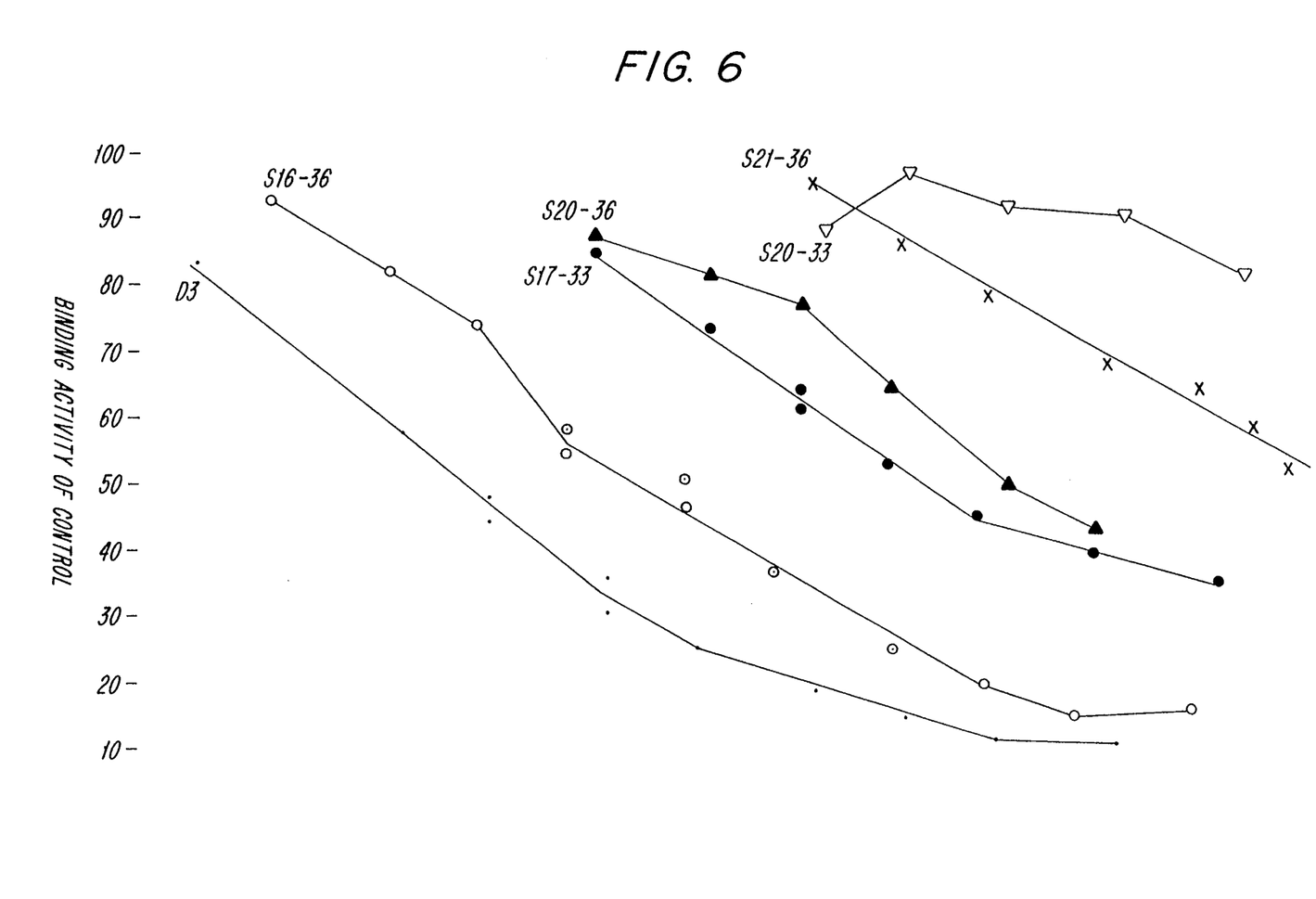

As T15–36 showed biological activity similar to that of D3, several synthetic peptides spanning this sequence were constructed (FIG. 2) and tested for biological activity (FIG. 6). Peptide S16–36, one residue shorter at the N-terminus than T15–36, elicited a 50% inhibition of fibronectin binding at a concentration of 10 nmol/ml compared to 3 nmol/ml for D3. Knowing that peptide TL17–36 retained biological activity, we constructed peptide S17–33 to test for the involvement of the C-terminal amino acids in fibronectin binding. It was found to have a markedly reduced but consistently observed biological activity, eliciting a 50% inhibition of fibronectin binding at a concentration of 100 nmol/ml. Further reduction in size of this peptide from the N-terminus producing S20–33 resulted in a near total loss of 
activity. However, expansion of peptide S20-33 from the C-terminus to produce S20-36 resulted in a peptide which had a level of activity comparable to that of S17-33, showing 50% inhibition at 200 nmol/ml. Peptide S21-36 still showed inhibition activity which was directly proportional to the amount of peptide, but was about 10-fold less effective than S20-36. We have, therefore, reduced the fibronectin binding region of D3 to a core peptide, S20-33, which is essential for activity but alone is not sufficient to inhibit binding. Addition of the sequence PSY to the N-terminus or LPK to the C-terminus resulted in peptides with similar biological activity. Any further reduction in the size of these peptides causes a large reduction in activity.

Adhesion of bacteria to fibronectin has been proposed as a virulence factor enabling bacteria to colonize wound tissues and blood clots (Ryden et al., 1983, JBC 258: 3396-3401; Proctor et al., 1982, JBC 257: 14788-14794); and the prevention of this interaction is an attractive target for either prophylaxis or vaccination studies. Some progress towards achieving this goal has been reported previously from studies of fibronectin binding by Treponema palladium (Thomas et al., 1985, J. Exp. Med., 14-25) and Trypanosoma cruzi. A monoclonal antibody that inhibits attachment of eukaryotic cells to fibronectin coated substrates also blocks the binding of fibronectin to Treponema palladium (Thomas et al., 1985a) and Trypanosoma cruzi (Ouaissi et al, 1986; J. Exp. Med., 162: 1715-1719). Binding was also prevented by the peptide RGDS, the amino acid sequence within the cell binding domain of fibronectin which is recognized by the eukaryotic fibronectin integrin receptors (Thomas et al., 1985b; J. Exp. Med. 162: 1715-1729; Ouaissi et al., 1986). This same peptide also blocked the attachment of spirochetes to cultured human cells. However, it must be considered that the RGDS peptide would also abrogate the role of fibronectin. Secondly, these microorganisms are unusual in their specificity for the cell binding domain of fibronectin.

The approach has been to characterize the interaction between fibronectin and the S. aureus receptor at the molecular level through the use of synthetic peptides.

Results from chemical modification of the D3 peptide indicate that glutamic and aspartic residues are essential for banding to fibronectin. This is of particular interest, as the motif of either FEEDT or DFEEDT appears in each of the three D-repeats of the S. aureus FN-receptor. In fact, in D3 this motif is repeated twice. Furthermore, sequence data obtained from genes coding for two fibronectin receptors of Streptococcus dysgalactiae each show three repeat sequences containing either DFTEDT (gene I) or EVEDT (gone II) motifs in each of the repeats (submitted for publication). Loss of activity upon cleavage with endoprotease Glu-c may be attributed to disruption of the FEEDT motif, and is further indication of the involvement of acidic amino acid residues.

The activity showed by the D3 tryptic digest product T15-36, and synthetic peptide S16-36 effectively localized the fibronectin binding determinant of D3 to the C-terminal half of the peptide which contains the FEEDT motif. It is interesting that the sequence IEEDT appears also near the N-terminus of D3 (residues 8-12) and that repeats D1 and D2 contain FEEDT at the same location. The presence of this motif repeated twice in D3 may account for its substantially higher biological activity in comparison to D1 and D2.

Attempts to further localize the fibronectin binding determinant within peptide S16-36 resulted in substantial losses of biological activity. We believe that peptide S20-33 contains the amino acid residues which establish contact with and bind to fibronectin. This peptide by itself shows essentially no activity. However, addition of the tripeptide PSY to the N-terminus (S17-33) or LPK to the C-terminus (20-36) resulted in a dramatic recovery of activity. If this core peptide were to have both flanking sequences, it would be one residue shorter at the N-terminus than peptide S16-36 which had a level of activity directly comparable to D3. Our chemical modification experiments indicated that neither tyrosine, nor lysine are involved in contacts with fibronectin. We propose that the PSY and LPK flanking tripeptides are not involved in contacts with fibronectin, but are required for the peptide to assume a proper and stable conformation. We note that loss of one amino acid from the N-terminus of S20-36 caused a greater than 10-fold reduction of activity.

The previous study of D3 and the ZZ-FR fusion protein (Signas et al., 1989), in combination with the present results, indicate that while a dramatic drop of activity occurs when the continuity of the three tandem D-repeats is disrupted, the change in activity when D3 is reduced to S17-36 is quite irrelevant. Further reduction in the size of S17-36 causes a loss in activity comparable to that observed through physical separation of the tandem repeats. Therefore, the secondary structure of the individual repeats provides one level of affinity for fibronectin, and the tertiary organization of the three repeats results in an affinity which is an order of magnitude higher. A third, hypothetical and as of yet unexplored, level of organization and further increase in affinity for fibronectin may be attained through the quaternary organization of fibronectin receptors on the cell surface of S. aureus 8325-4.

TABLE 1

Amino Acid Composition of Peptide D3, and of its Derivatization Products

| | Amino acid residues per 1,000 | | | |
|---|---|---|---|---|
| | Unmodified | DHP—K[2] | Gly—OCH$_3$[2] | TNM—Y[3] |
| Asx* | 217.7 (189.2) | 226.8 | 155.9 | 157.1 |
| Glx* | 156.3 (162.2) | 193.4 | 138.4 | 174.9 |
| Ser | 51.4 (54.1) | 58.7 | 44.7 | 57.7 |
| Gly* | 54.6 (54.1) | 62.7 | 292.7 | 64.6 |
| His | 57.4 (54.1) | 65.8 | 43.5 | 46.6 |
| Arg | — | — | — | — |
| Thr | 82.7 (81.1) | 95.3 | 76.9 | 100.0 |
| Ala | — | — | — | — |
| Pro | 54.5 (54.1) | 63.5 | 49.9 | 60.4 |
| Tyr* | 18.2 (27.0) | 23.4 | 10.5 | 0.9 |
| Val | 51.6 (54.1) | 61.6 | 39.3 | 57.1 |
| Met | — | — | — | — |
| Cys | — | — | — | — |
| Ile | 29.3 (54.1) | 33.8 | 26.8 | 31.8 |
| Leu | 30.6 (27.0) | 33.5 | 22.2 | 32.8 |
| Phe | 70.2 (81.1) | 55.0 | 57.6 | 72.1 |
| Lys* | 107.9 (108.1) | 2.4 | 89.2 | 100.9 |

Amino acids either targeted for, or affected by, chemical modification are indicated by asterisks. Numbers in brackets refer to the expected values, based on the known composition of D3.
[1]Dihydroxypropylation - reduction of lysine
[2]Conversion of aspartic and glutamic residues to glycine methyl esters
[3]Tetranitromethane oxidation of tyrosine The present fibronectin binding peptide can be used for immunization, whereby the peptide, preferably in combination with a fusion-protein to create a large antigen to respond to, is injected in dosages causing immunological reaction in the host mammal. Th 
of ruminants against mastitis caused by Staphylococcal infections.

Further, the fibronectin binding peptide can be used to block an infection in an open skin wound by wound treatment using the fibronectin binding peptide in a suspension. Thus the fibronectin binding peptide can be used for the treatment of wounds, e.g. for blocking protein receptors, or for immunization (vaccination). In the latter case the host body produces specific antibodies, which can protect against invasion of bacterial strains comprising such a fibronectin binding peptide. Hereby the antibodies block the adherence of the bacterial strains to damaged tissue.

Examples of colonizing of a tissue damage are:

a) colonizing of wounds in skin and connective tissue, which wounds have been caused by a mechanical trauma, chemical damage, and/or thermical damage;

b) colonizing of wounds on mucous membranes, such as in the mouth cavity, or in the mammary glands, urethra, or vagina;

c) colonizing on connective tissue proteins, which have been exposed by a minimal tissue damage (microlesion) in connection with epithelium and endothelium (mastitis, heart valve infection, hip exchange surgery).

When using the present FNBP, or the peptide, for the purpose of immunization (vaccination) in mammals, including man, the peptide is dispersed in sterile, isotonic saline solution, optionally while adding a pharmaceutically acceptable dispersing agent. Different types of adjuvants can further be used in order to sustain the release in the tissue, and thus expose the peptide for a longer time to the immundefense system of a body.

A suitable dosage to obtain immunization is 0.5 to 5 ug of peptide, per kg bodyweight and injection of immunization. In order to obtain a durable immunization, vaccination should be carried out on more than one consecutive occasion with an interval of 1 to 3 weeks, preferably on three occasions.

When using the present peptide for topical or local administration the protein is dispersed in an isotonic saline solution to a concentration of 25 to 250 ug per ml. The wounds are then treated with such an amount only to obtain a complete wetting of the wound surface. For an average wound thus only a couple of milliliters of solution are used in this way. After treatment using the peptide solution the wounds are suitably washed with isotonic saline or another suitable wound treatment solution.

Further the fibronectin binding peptide as well as the minimal fibronectin binding site peptide of the present invention can be used to diagnose bacterial infections caused by Staphylococci strains, whereby a fibronectin binding peptide of the present invention is immobilized on a solid carrier, such as small latex or Sepharose® beads, whereupon sera containing antibodies are allowed to pass and react with the FNBP thus immobilized. The agglutination is then measured by known methods.

Further, the peptide can be used in an ELISA test (Enzyme Linked Immuno Sorbent Assay; E. Engvall, Med. Biol. 55, 193, (1977)). In such a test, wells in a polystyrene microtitre plate are coated with the FNBP, and incubated over night at 4' C. The plates are then thoroughly washed using PBS containing 0.05% TWEEN 20, and dried. Serial dilution of the patient serum was made in PBS-Tween, added to the wells, and incubated at 30° C. for 1.5 hrs. After rinsing antihuman-IgG conjugated with an enzyme, or an antibovine-IgG conjugated with an enzyme, respectively, horse radish peroxidase or an alkaline phosphatase was added to the wells and incubated at 30° C. for 1.5 hrs, where upon when the IgG has been bound thereto, and after rinsing, an enzyme substrate is added, a p-nitrophosphate when an alkaline phosphatase was added, or orthophenylene diamine substrate (OPD) when a peroxidase has been used, respectively. The plates comprising the wells were thus then rinsed using a citrate buffer containing 0.055% OPD, and 0.005% $H_2O_2$, and incubated at 30° C. for 10 min. Enzyme reaction was stopped by adding a 4N solution of $H_2SO_4$ to each well. The colour development was measured using a spectrophotometer.

Depending on the type of enzyme substrate used a fluoroscense measurement can be used as well.

Another method to diagnose Staphylococci infections is by using the DNA gene probe method based on the peptide sequence. Thereby the natural or synthetic DNA sequences are attached to a solid carrier, such as a polystyrene plate as mentioned above, by, e.g., adding a milk in the case of diagnozing a mastitis to the surface. The DNA gone probe, optionally labelled enzymatically, or by a radioactive isotope is then added to the solid surface plate comprising the DNA sequence, whereby the DNA gene probe attaches to the sequence where appearing. The enzyme or the radioactive isotope can then readily be determined by known methods.

BRIEF DESCRIPTION OF THE DRAWINGS

FIG. 1 illustrates the amino acid sequences of the tandem repeats constituting the fibronectin binding site of the *S. aureus* 8325-5 FnBP.

FIG. 2 illustrates the effect of chemical modification on the ability of peptide D3 to inhibit binding of $^{125}$I-HFN to *S. aureus* 8325-4 FnBP.

FIG. 3 illustrates reverse-phase HPLC of peptide D3 before (panel a) and after (panel b) digestion with trypsin, and also provides a profile of trypsin alone (panel c).

FIG. 4 illustrates an assay for ability of peptide D3 to inhibit binding of $^{125}$I-HFN or $^{125}$I-29 kDa fragment of HFN to *S. aureus* 8325-4 under various conditions.

FIG. 5 illustrates an assay for the ability of purified protease cleavage products to inhibit binding of $^{125}$I-HFN to *S. aureus* 8325-4.

FIG. 6 illustrates an assay for the ability of synthetic peptides to inhibit binding of $^{125}$I-HFN to cells of *S. aureus* 8325-4.

FIGURE LEGENDS

FIG. 1

Amine acid sequence of the tandem repeats constituting the fibronectin binding site of the *S. aureus* 8325-5 FnBP. Synthetic peptides corresponding to each of the repeats have been named D1, D2, and D3 [SEQ ID Nos. 2–4]. Beneath the sequence of D3 is illustrated the composition of several proteolytic cleavage products of the D3 peptide, and of smaller synthetic peptides which were used to further define the fibronectin binding determinant of D3. Two numbers preceded by one or two letters is used to identify the individual peptides. The numbers refer to the position of the N- and C-terminal residues of each peptide within the 37 amine acid sequence of D3. The letters V, C, and T indicate cleavage products isolated from endoprotease Glu-c, trypsin, or chymotrypsin digests, respectively, of peptide D3. Peptide T15–36 was subjected to a second digestion with either lysine endopeptidase-c producing TL17–36, or with endoprotease Glu-c producing TV15–30. The letter S is used to designate peptides generated through chemical synthesis.

FIG. 2

Effect of chemical modification on the ability of peptide D3 to inhibit binding of $^{125}$I-HFN to *S. aureus* 8325-4. The indicated amount of peptide was mixed with $5 \times 10^8$ cells and $5 \times 10^4$ cpm of $^{125}$I-HFN in an assay volume of 0.5 ml of PBX supplemented with 0.1% (wt/vol) bovine serum albumin, 0.1% (vol/vol) Tween 80, and 0.02% (wt/vol) sodium azide. After 60 min. of end-over-end mixing at room temperature, unbound fibronectin was diluted by addition of 3 ml of ice cold PBS containing 0.1% (vol/vol) Tween 80. After centrifugation at 1,350 x g for 20 min., the supernatant was aspirated and the radioactivity associated with the bacterial pellet was quantitated on a LKB gamma counter.

Panel A: Inhibitory activity of unmodified D3 (—), and after modification on tyrosine (Δ—Δ), or lysine (o—o) residues.

Panel B: Inhibitory activity of unmodified D3 (—), and after modification of carboxylic side residues with glycine methyl ester (o—o), ethanolamine (Δ—Δ), or the EDC reagent alone (□—□).

FIG. 3

Reverse-phase HPLC of peptide D3 before (Panel A), and after (Panel B) digestion with trypsin. The chromatography was performed using a Vydac $C_{18}$ analytical column and TFA buffered acetonitrile as the eluent at a flow rate of 1 ml/min. The numbers above the peaks identify the first and last residues of the cleavage products within the sequence of D3. Panel C is a profile of trypsin alone.

FIG. 4

Assay for ability of peptide D3 to inhibit binding of $^{125}$I-HFN or $^{125}$I-29 kDa fragment of HFN to *S. aureus* 8325-4 either before (Δ—Δ), or after (o—o) complete digestion with trypsin (A,D), chymotrypsin (B,E) or endoprotease Glu-c (C,F).

FIG. 5

Assay for the ability of purified protease cleavage products to inhibit binding of $^{125}$I-HFN to *S. aureus* 8325-4. The $^{125}$I-HFN bound by cells in the absence of peptide was designated as 100%, and binding in the presence of peptides was expressed relative to this value.

FIG. 6

Assay for ability of synthetic peptides to inhibit binding of $^{125}$I-HFN to cells of *S. aureus* 8325-4. Assay conditions were as described in the legend to FIG. 2. The sequences of the peptides are illustrated in FIG. 1. The results are expressed as a percentage of the fibronectin bound by cells in the absence of peptide.

We claim:

1. Fibronectin binding peptide consisting of the structure [SEQ ID NO. 1]R'-PSYQFGGHNS VDFEEDT-R² wherein R' is hydrogen, K or DK, and R² is hydroxy, L, LP or LPK.

* * * * *